United States Patent [19]

Kubo et al.

[11] Patent Number: 4,788,321

[45] Date of Patent: Nov. 29, 1988

[54] PERFLUOROALKENYLOXYBENZOIC ACID DERIVATIVE, PROCESS FOR PREPARING THE SAME AND PREPOLYMER OF THE DERIVATIVE

[75] Inventors: Motonobu Kubo, Toyonaka; Sinji Tamaru, Suita, both of Japan

[73] Assignee: Daikin Industries, Ltd., Osaka, Japan

[21] Appl. No.: 138,398

[22] Filed: Dec. 28, 1987

[30] Foreign Application Priority Data

Dec. 29, 1986 [JP] Japan .................................. 61-311326
Feb. 25, 1987 [JP] Japan .................................. 62-43549

[51] Int. Cl.$^4$ ............................................. C07C 69/76
[52] U.S. Cl. .......................................................... 560/65
[58] Field of Search .......................................... 560/65

[56] References Cited

U.S. PATENT DOCUMENTS 4,642,368  2/1987  Hofmeister et al. ................. 560/65

FOREIGN PATENT DOCUMENTS 9031725  2/1984  Japan .
1024547  2/1986  Japan .

*Primary Examiner*—Paul J. Killos
*Attorney, Agent, or Firm*—Armstrong, Nikaido, Marmelstein & Kubovcik

[57] ABSTRACT

The present invention provides a perfluoroalkenyloxybenzoic acid derivative of the formula

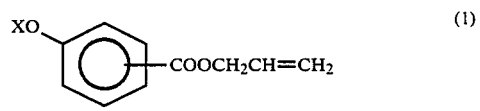

(1)

wherein X is perfluoroalkenyl group having 6 to 14 carbon atoms, and process for preparing the same.

Further, the present invention provides a prepolymer of a perfluoroalkenyloxybenzoic acid derivative comprising a repeating unit of the formula

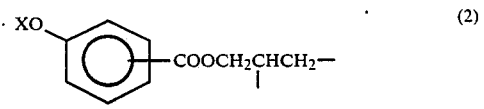

(2)

wherein X is same as above, and a repeating unit having one double bond and derived from the cleavage of double bond of a diene compound.

6 Claims, No Drawings

PERFLUOROALKENYLOXYBENZOIC ACID DERIVATIVE, PROCESS FOR PREPARING THE SAME AND PREPOLYMER OF THE DERIVATIVE

The present invention relates to a novel fluorine-containing aromatic carboxylic acid derivative, more particularly to perfluoroalkenyloxybenzoic acid derivative, process for preparing the same and a prepolymer of the derivative. The present perfluoroalkenyloxybenzoic acid derivative is useful as a starting material for a novel thermoplastic or thermosetting resin having resistances to water and heat, modifier for allyl resin or alkyd resin and the like.

Conventionally, as a perfluoroalkenyloxybenzoic acid derivative, is known the compound having the following formula, which is disclosed in Japanese patent specification (Tokkyo Kokoku) No. 19712/1983.

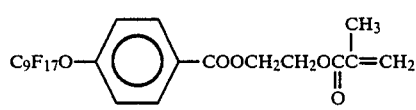

The compound is a benzene derivative substituted by a perfluoroalkenyloxy group and a group having an unsaturated bond. Also, the specification discloses a benzene derivative having similar substituents of the following formula.

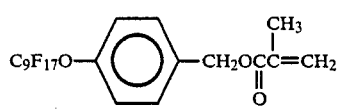

These compounds are used as a modifier for diallyl phthalate resin and like allyl resins and afford a modified cured product of allyl resin having superior water resistance. However, the cured product has a defect of being inferior in heat resistance.

Generally, diallyl aromatic dicarboxylate such as diallyl phthalate is a monomer having two polymerizable functional groups which is finally fabricated into a thermosetted article. In the process for fabricating an end molded article from such a monomer, it is usually coducted to suspend the polymerization reaction to obtain so low-molecular-weight a polymer as to have solubility in a solvent or thermoplasticity. The polymer is molded in the form of a solution or a thermoplastic polymer and polymerized after molding or along with the molding to a cured polymer which is neither soluble in any solvent nor molten. In the process, such a polymer as to have solubility or thermoplasticity is called as a prepolymer.

A cured article of a conventional prepolymer obtained from diallyl phthalate or the like is useful as a socket, connector and like electric parts, laminates, decorative sheets, etc., but has a defect of being poor in water-resistance.

An object of the invention is to provide a novel perfluoroalkenyloxybenzoic acid derivative and process for preparing the same, the derivative being useful as a modifier for giving good resistances to water and heat to allyl resins, and able to polymerize by itself or together with other compounds having a double bond.

Another object of the invention is to provide a novel prepolymer of perfluoroalkenyloxybenzoic acid derivative which affords a cured product having an excellent water-resistance.

The above and other objects of the invention will become apparent from the following description.

The present invention provides a perfluoroalkenyloxybenzoic acid derivative of the formula

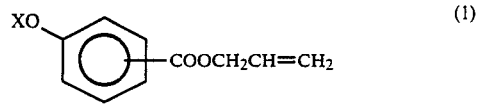

wherein X is perfluoroalkenyl group having 6 to 14 carbon atoms, and process for preparing the same.

Further, the present invention provides a prepolymer of a perfluoroalkenyloxybenzoic acid derivative comprising a repeating unit of the formula

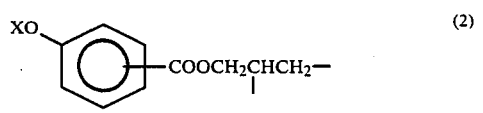

wherein X is perfluoroalkenyl group having 6 to 14 carbon atoms, and a repeating unit having one double bond and derived from the cleavage of double bond of a diene compound.

Examples of perfluoroalkenyl groups X having 6 to 14 carbon atoms of the invention are the following groups of the formulae

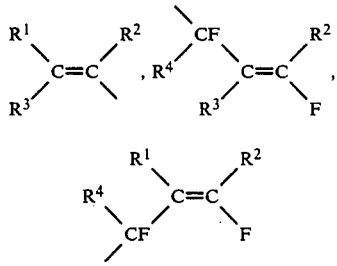

wherein $R^1$, $R^2$ and $R^3$ are each perfluoroalkyl group having 1 to 6 carbon atoms, or one of them is fluorine atom and the others are each perfluoroalkyl group having 1 to 6 carbon atoms, $R^4$ is perfluoroalkyl group having 1 to 5 carbon atoms. Especially preferable are groups formed by eliminating one fluorine atom from a dimer or trimer of hexafluoropropene, or tetramer, pentamer, hexamer or heptamer of tetrafluoroethylene. These groups are shown below by the formulae.

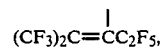

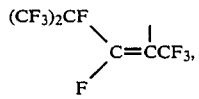

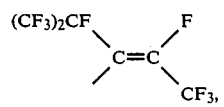

-continued

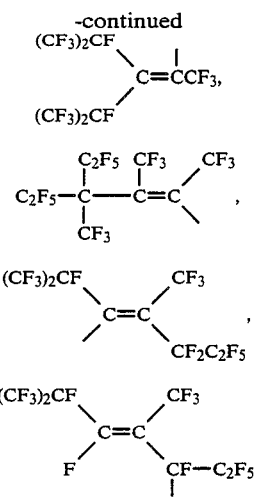

In the invention, the repeating unit of the formula (2) is derived from a perfluoroalkenyloxybenzoic acid derivative represented by the formula

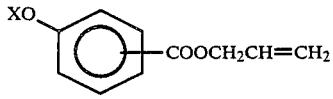

where X is same as above.

The above perfluoroalkenyloxybenzoic acid derivative (1) includes all of isomers in which OX group is bonded to ortho, meta or para position of the 2-propenyloxycarbonyl group.

The perfluoroalkenyloxybenzoic acid derivative of the invention can be prepared, for example, by reacting an allyl alcohol with a perfluoroalkenyloxybenzoic acid of the formula

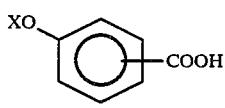

wherein X is perfluoroalkenyl group having 6 to 14 carbon atoms. The compound (3) is a known compound. The reaction is conducted preferably in a solvent. As a solvent is preferably used one which make an azeotrope with water and is substantially immiscible with water. Examples thereof are benzene, toluene, xylene, diallyl ether, etc. Allyl alcohol is used preferably in an amount of about 1 to 20 moles per mole of the compound (3). The reaction temperature is suitably selected but is usually about 50° to 200° C., preferably about 70° to 160° C. The reaction is conducted preferably in the presence of a known esterification catalyst such as sulfuric acid, hydrochloric acid, phosphoric acid, trifluoroacetic acid or boron trifluoride ethyl etherate. The catalyst is used preferably in an amount of about 0.01 to 30 wt% based on the compound (3). In the reaction, p-methoxyphenol, hydroquinone, tert-butyl-catechol and like radical polymerization inhibitor may be added in a small amount. The amount is preferably about 0.01 to 5 wt% based on allyl alcohol.

Further, the present compound (1) can also be prepared by reacting allyl chloride with the compound (3) in the presence of triethylamine or like tertiary amine.

The similar reaction conditions are used with respect to a solvent, reaction ratio, reaction temperature, polymerization inhibitor, etc. The desired compound (1) can be separated and recovered by known methods used in the separation of a mixture of organic compounds and liquid. For example, the desired compound (1) can be recovered by concentration, distillation or gas chromatography.

The present compound (1) is further prepared by reacting a perfluoroalkene XF with allyl hydroxybenzoate of the formula

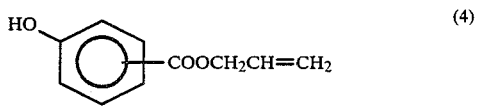

In the above, X is perfluoroalkenyl group having 6 to 14 carbon atoms.

The above compound (4) is obtained by reacting allyl alcohol with hydroxybenzoic acid. The reaction is conducted in the similar manner as in the reaction of allyl alcohol and the above compound (3).

Examples of perfluoroalkenes XF are the following compounds of the formula

wherein $R^1$, $R^2$ and $R^3$ are each perfluoroalkyl group having 1 to 6 carbon atoms, or one of them is fluorine atom and the others are each perfluoroalkyl group having 1 to 6 carbon atoms. Especially preferable are a dimer or trimer of hexafluoropropene, or tetramer, pentamer, hexamer or heptamer of tetrafluoroethylene. These are shown below by the formulae.

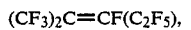

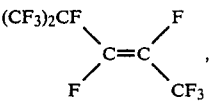

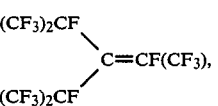

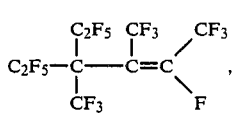

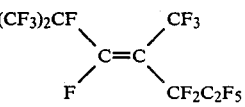

The reaction is conducted preferably in a solvent in the presence of a base. Examples of bases are triethylamine, trimethylamine, tripropylamine or like amines, alkali metal or hydroxides thereof, etc. As a solvent is used preferably an aprotic polar solvent such as acetonitrile, dimethyl formamide, dimethyl surfoxide, etc. The perfuluoroalkene is used preferably in an amount of about 1 to 10 moles per mole of the compound (4). The reaction temperature is suitably selected but is usually about 0° to 40° C., preferably about 0° to 20° C. The base is used preferably in an amount of about 1 to 20 moles per mole of the compound (4). The desired compound (1) can be separated and recovered by known methods used in the separation of a mixture of organic compounds and liquid. For example, the reaction mixture is added to a large amount of diluted hydrochloric acid and the resulting precipitates are collected and is distilled at a reduced pressure to obtain the desired compound.

The compounds XF of the formula (5) include compounds represented by the formulae below.

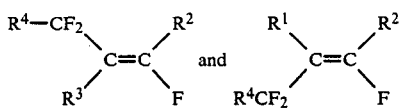

From the above compounds, the following groups are produced respectively:

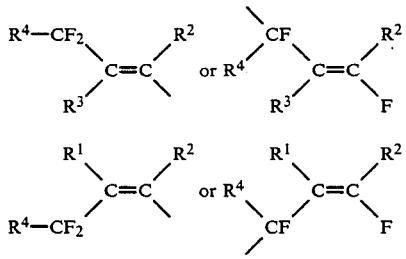

More specifically, from the compound

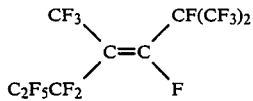

the following group is formed.

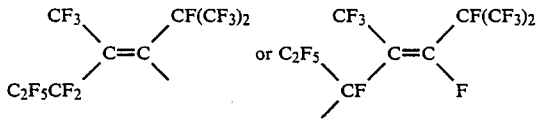

The present compound can be polymerized by heating in the presence of a peroxide such as benzoyl peroxide, thereby a polymer is prepared. The polymer is a thermoplastic resin and excellent in resistances to water and heat. The present compound can be copolymerized with other polymerizable compounds such as diallyl phthalate, diallyl isophthalate or diallyl terephthalate to form a prepolymer, the prepolymer being able to afford a cured product having water-resistance. Further, the present compound can be mixed with a prepolymer of diallyl phthalate, diallyl isophthalate, diallyl terephthalate, etc. and the mixture is cured to obtain a product having water-resistance.

The present invention also provides a prepolymer of a perfluoroalkenyloxybenzoic acid derivative comprising a repeating unit of the above formula (2) and a repeating unit having one double bond and derived from the cleavage of double bond of a diene compound.

Examples of repeating unit having one double bond and derived from the cleavage of a double bond of a diene compound are those obtained by the cleavage of a double bond of various compounds such as butadiene, isoprene, chloroprene, diallyl phthalate, diallyl isophthalate or diallyl terephthalate.

The present prepolymer includes a copolymer having other repeating unit in addition to the repeating unit of the formula (2) and the repeating unit derived from a diene compound.

Examples of other repeating units are those derived from cleavage of double bond of various compounds such as ethylene, vinyl acetate, vinyl fluoride, vinyl chloride, acrylamide, methacrylamide, styrene, α-methylstyrene, p-methylstyrene, alkyl ester of acrylic acid or methacrylic acid, benzyl (meth)acrylate, vinyl alkyl ether, halogenated alkyl vinyl ether, vinyl alkyl ketone, cyclohexyl (meth)acrylate or maleic anhydride.

The prepolymer has a number average molecular weight preferably of about 1000 to 50000, more preferably about 3000 to 10000. With so great in molecular weight, the prepolymer is hardly processed. With too small in molecular weight, the cured product does not have practical strength. The prepolymer has an iodine value (gram of iodine which adducts to 100 g of sample) preferably of about 10 to 95, more preferably about 25 to 80. The prepolymer having too small iodine value can not afford a cured product having practical strength. A cured product having superior impact-resistance is hardly obtained from the prepolymer having too large iodine value.

In the present invention, the prepolymer contains the repeating unit (2) in an amount preferably of at least about one percent (weight percent, same as hereinafter), more preferably at least about 10%. With less than about one percent, water-resistance is not expected. The prepolymer contains the repeating unit having one double bond and derived from the cleavage of a double bond of a diene compound preferably in such an amount that the prepolymer has an iodine value of at least about 10, more preferably at least about 25. The prepolymer having too small iodine value hardly affords a cured product having practical strength.

The present prepolymer can be obtained by copolymerizing the above compound (1).

The diene compounds include butadiene, isoprene, chloroprene or like conjugated diene compound, diallyl phthalate, diallyl isophthalate, diallyl terephthalate or like non-conjugated diene compound, and other polymerizable compounds.

Further, in addition to these diene compounds, it is possible to copolymerize an ethylenically unsaturated compound such as ethylene, vinyl acetate, vinyl fluoride, vinyl chloride, acrylamide, methacrylamide, styrene, α-methylstyrene, p-methylstyrene, alkyl ester of acrylic acid or methacrylic acid, benzyl (meth)acrylate, vinyl alkyl ether, halogenated alkyl vinyl ether, vinyl alkyl ketone, cyclohexyl (meth)acrylate or maleic anhydride.

Although the present prepolymer has already been explained in its structural feature, detailed structures of its individual parts can not be shown by a single structural formula since various formulae are considered depending on the propagation, termination or chain transfer reaction of the polymerization. For example, when the radical polymerization was conducted with use of allyl p-perfluorononenyloxybenzoate as the compound of the formula (1) and diallyl terephthalate as a copolymerizable monomer, the following several kinds of structures are formed in mixture. Allyl groups in the monomers form a carbon-carbon molecular bond such as a head-to-tail structure (A) or head-to-head structure (B) shown below.

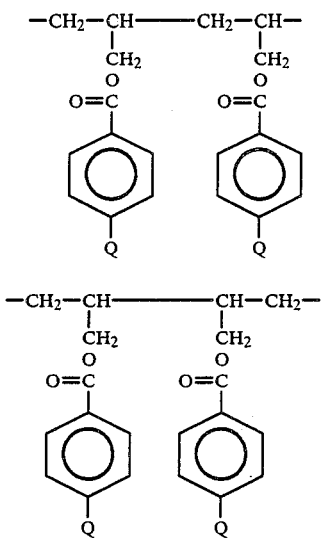

Q is $-OC_9F_{17}$, $-COOCH_2CH=CH_2$ or $-COO$
$\quad\quad\quad\quad\quad\quad\quad\quad\quad\quad\quad\quad\quad\quad\quad\quad\quad\quad\quad\quad$ |
$\quad\quad\quad\quad\quad\quad\quad\quad\quad\quad\quad\quad\quad\quad\quad\quad\quad\quad\quad\quad$ $CH_2$
$\quad\quad\quad\quad\quad\quad\quad\quad\quad\quad\quad\quad\quad\quad\quad\quad\quad\quad\quad\quad$ |
$\quad\quad\quad\quad\quad\quad\quad\quad\quad\quad\quad\quad\quad\quad\quad\quad$ ~CH—CH$_2$~

The repeating unit having one double bond derived from cleavage of double bond of a diene compound include (a) when the double bonds are non-conjugated, a repeating unit obtained by cleavage of one double bond to form an addition bond and thereby the other double bond remains as not cleaved, (b) when the double bonds are conjugated, (1) a repeating unit obtained by cleavage of one double bond to form an addition bond and thereby the other double bond remains as not cleaved, and (2) a repeating unit obtained by cleavage of two double bonds and thereby two double bonds shift to the adjacent position to form one double bond, the position being between the intermediate two carbon atoms of four carbon atoms constituting two double bonds.

Further, the prepolymer has a terminal formed by hydrogen abstraction and shown by the structure (C) or a terminal formed by disproportionation between terminal radicals and shown by the structure (D), etc.

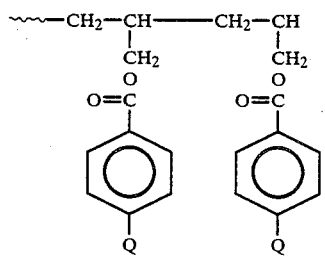

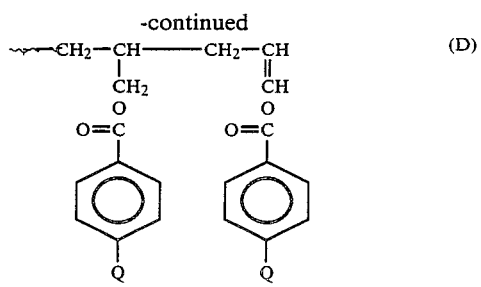

In the polymerization, methods and conditions thereof are suitably selected. For example, as radical polymerization are adopted bulk polymerization, solution polymerization, suspension polymerization, emulsion polymerization, etc. As ionic polymerization are conducted cationic polymerization, etc. As an initiator in radical polymerization is used a compound which produces free radicals. Preferred radical initiators are benzoyl peroxide, tert-butyl perbenzoate, acetyl benzoyl peroxide, succinyl peroxide, diisopropyl peroxydicarbonate, ammonium persulfate and like peroxides, azobisisobutyronitrile and like azonitriles, etc. Further, it is possible to to use a chain transfer agent which is disclosed in Japanese Examined Patent Publication No. 16,035/1960 and has the formula $$(R)_m\text{—}\underset{(Cl)_n}{\overset{CH_2Z}{\bigcirc}}$$

wherein Z is Cl, OH or group convertible to OH, R is lower alkyl (1 to 4 carbon atoms), m is 0 to 4, n is 0 to (4-m). The chain transfer agent is used in an amount of preferably about 10 to 25% by weight in order to adjust the molecular weight and to prevent the gelation. For the same purpose are adjusted amount of initiator, polymerization temperature, polymerization time, etc. The radical initiator is used in an amount of 0.1 to 10% by weight based on the weight of monomers. However, the amount of initiator is not limited thereabove and is suitably selected depending on polymerization degree of the desired polymer, polymerization time, polymerization temperature, etc. The polymerization temperature is usually $-80°$ C. to $+250°$ C. as depending on the decomposition temperature of the initiator. Generally, the temperature is preferably in the range of $-40°$ C. to $+150°$ C. Solvents useful for solution polymerization are benzene, toluene, xylene and like aromatic hydrocarbons, chloroform, methylene chloride, ethylene chloride and like low-basic solvents. These solvents are used singly or in mixture. The cationic polymerization is preferably conducted in a solvent such as toluene, benzene, etc. at $-30°$ C. to $+250°$ C. in the presence of boron trifluoride ethyl etherate, aluminum chloride or like initiator.

The polymer is separated from the reaction mixture by a usual method, for example, by adding the mixture to a poor solvent which does not dissolve the polymer such as methanol, diisopropyl ether, dimethyl ether, petroleum ether or n-hexane. The polymer is obtained as precipitates. The precipitated polymer is purified by dissolving it in a solvent which is cabable of dissolving the polymer such as acetone, methyl ethyl ketone, ethyl acetate, dioxane, tetrahydrofuran, ethylene dichloride, chloroform, carbon tetrachloride, trichloroethylene, benzene, toluene, etc. and thereafter re-precipitating the polymer by adding the solution in a poor solvent.

The present prepolymer can be cured by itself or in the form of a mixture thereof with a prepolymer of diallyl phthalate, diallyl isophthalate, diallyl tetraphthalate, etc. The curing is conducted by heating or light in the presence of thermal polymerization initiator, photopolymerization initiator, etc. or with irradiation of electron rays, gamma-ray or like active energy rays in the absence of the initiator. In case of using the initiator, as a carrier for initiator is used diallyl phthalate, diallyl isophthalate, diallyl terephthalate or like monomer. The carrier is used preferably up to about 90% by weight of the mixture.

Examples of thermal polymerization initiators are methyl ethyl ketone peroxide, cyclohexanone peroxide and like ketone peroxides, t-butyl perbenzoate, t-butyl peroxy-2-ethylhexoate and like peresters, t-butyl hydroperoxide, cumene hydroperoxide and like hydroperoxides, benzoyl peroxide and like diacyl peroxides. The photopolymerization initiators include 2,2-diethoxyacetophenone, 2,2-dimethoxy-2-phenylacetophenone and like acetophenones, benzophenone and like ketones, 2-chloro-thioxanthone and like thioxanthones, etc. The initiator is used preferably in an amount of about 0.001 to 20% by weight, more preferably about 0.1 to 10% by weight based on the total amount of the prepolymer and carrier.

The curing is conducted usually at a temperature from room temperature to 250° C., preferably from room temperature to 180° C., despite that any of heat, light or active energy rays is used.

The prepolymer contains a carbon-carbon double bond in the main vhain or side chain, exhibits cross-linking ability and affords a cured product. Further, the prepolymer has a perfluoroalkenyloxy chain as the other side chain which gives an excellent water-resistance to the cured product. The cured product obtained from the present prepolymer has water-resistance which is much superior to that of a cured product prepared from the conventional diallyl phthalate. Even the prepolymer containing about 50% by weight of the repeating unit (1) provides a curing product which is about 1/10 in water absorbency than the conventional product.

The invention will be described below with reference to Examples and Comparison Examples.

EXAMPLE 1

Into a reaction vessel equipped with a stirrer, dropping funnel and thermometer were placed 276 g (2 moles) of p-hydroxybenzoic acid, 2.5 l of dimethylformamide and 606 g (6 moles) of triethylamine and the mixture was cooled below 20° C. Thereto added dropwise 900 g (2 moles) of hexafluoropropene trimer over a period of about 30 minutes and the mixture was stirred for 4 hours while maintaining the temperature below 20° C. The mixture was poured dropwise into a large amount of a diluted aqeuous solution of hydrochloric acid while vigourously stirring the solution to obtain while precipitates. The precipitates were filtered, washed with water and dried. Into a reaction vessel equipped with a stirrer, water separator and condenser were placed 113.6 g (0.2 mole) of the resulting p-perfluorononenyloxybenzoic acid, 34.8 g (0.6 mole) of allyl alcohol, 500 ml of toluene, 1.5 g of sulfuric acid and 0.2 g of p-methoxyphenol. The mixture was mildly heated and refluxed.

A mixture of toluene and water was distilled off and cooled with a condenser, and toluene was separated from water and returned continuously to the reaction vessel. The mixture was heated for 20 hours and then allowed to cool. To the reaction mixture was added 200 ml of toluene and the solution was washed with a saturated aqeuous solution of sodium carbonate and then washed repeatedly with a saturated aqueous solution of sodium chloride until the aqueous layer did not indicate acidic. Toluene layer was concentrated and the resulting concentrate was distilled at a reduced pressure to collect a fraction boiling at 127°–128° C./7 mmHG which gives 91 g of allyl p-perfluorononenyloxybenzoate.

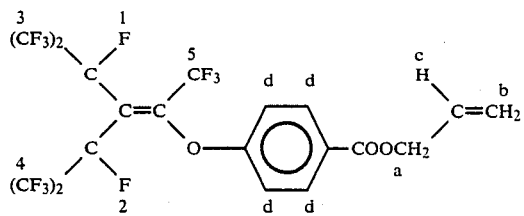

$^1$H—NMR (TMS standard, in CDCl$_3$, δ ppm)

a  4.8~4.9, m, 2H b  5.2~5.5, m, 2H c  5.8~6.3, m, 1H d  6.9~7.0, 7.9~8.1, 4H $^{19}$F—NMR (external standard CF$_3$COOH, in CDCl$_3$, δ ppm)
Chemical shift (δ ppm) is shown in which high magnetic field is indicated by a plus value.

1  + 79.3, 1F

2  +90.5, 1F

3  −6.2, 6F

4  −7.4, 6F

5  −22,5, 3F

EXAMPLE 2

A 86 g-quantity of allyl m-perfluorononenyloxy-benzoate was obtained as a fraction boiling at 126°–129° C./7 mmHg in the same manner as in Example 1 except that m-hydroxybenzoic acid was used in place of p-hydroxybenzoic acid.

Elementary analysis (C$_{19}$H$_9$F$_{17}$O$_3$) Theor.; C37.52%, H1.49%, F53.10%. Found; C37.01%, H1.50%, F52.88%.

EXAMPLE 3

Into a reaction vessel equipped with a stirrer, dropping funnel and thermometer were placed 27.6 g (0.2 mole) of p-hydroxybenzoic acid, 200 ml of methylene chloride and 60.6 g (0.6 mole) of triethylamine. Thereto added dropwise 250 ml of ethyl ether solution containing 66 g (0.22 mole) of hexafluoropropene dimer over a period of about 30 minutes and the mixture was stirred for 4 hours while maintaining the temperature below 20° C. The mixture was washed with a diluted aqueous solution of hydrochloric acid, and with a saterated aqueous solution of sodium chloride, and then dried on anhydrous sodium sulfate. Ether, was removed by distillation. To the residue were added 34.8 g (0.6 mole) of allyl alcohol, 500 ml of toluene, 1.5 g of sulfuric acid and 0.2 g of p-methoxyphenol. The mixture was mildly heated and refluxed. A mixture of toluene and water was distilled off and cooled with a condenser, and toluene was separated from water and returned continuously to the reaction vessel. The mixture was heated for 20 hours and then allowed to cool to room temperature. To the reaction mixture was added 200 ml of toluene and the solution was washed with a saturated aqueous solution of sodium carbonate and then washed with a saturated aqeuous solution of sodium chloride. Toluene was removed at a reduced presssure and the residue was distilled to collect a fraction boiling at 115°–118° C./8 mmHg which gives 45 g of allyl p-perfluorononenyloxybenzoate.

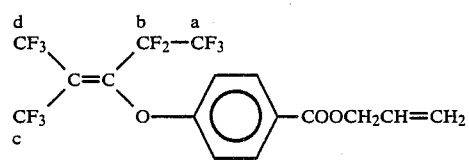

$^{19}$F—NMR (external standard CF$_3$COOH, in CDCl$_3$, δ ppm)

a  +4.2, 3F b  +35.0, 2F c  −17.9, 3F d  −21.3, 3F

EXAMPLE 4

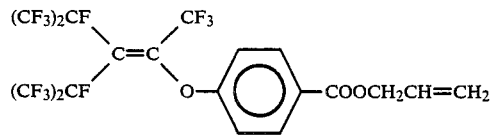

Into a vessel equipped with a stirrer and condenser were placed Compound A (750 g), diallyl terephthalate (250 g), benzoyl peroxide (14 g), dibutyltin dilaurate (12 g) and water (500 ml), and the mixture was reacted at 85° C. for 5 hours. After completion of the reaction, the mixture was cooled to room temperature and acetone (100 g) was added thereto. The organic layer was added dropwise to a large amount of methanol with stirring. The resulting precipitates were filtered, washed with methanol and dried at a reduced pressure to obtain 293 g of white powder. The powder was 25 in iodine value, 7.6×10$^3$ in number average molecular weight ($\overline{Mn}$), 9.1×10$^4$ in weight average molecular weight ($\overline{Mw}$) in term of polystyrene with use of gel permeation chromatography and 28.0 wt% in fluorine content. Accordingly, the above white powder was a prepolymer in which Compound A and diallyl terephthalate were contained in molar ratio of 1:2.2. To a solution of the prepolymer (70 parts) and diallyl terephthalate (30 parts) was added benzoyl peroxide (2 parts) and the mixture was stirred homogeneously. The mixture was poured into a Petri dish having internal diameter of 50 mm and heated at 95° C. for 10 hours to obtain a casting plate which was 50 mm in diameter and 3 mm in thickness.

EXAMPLE 5

White powder (288 g) was obtained in the same manner as in Example 4 except that Compound A (500 g) was used and 500 g of diallyl phthalate was used in place of diallyl terephthalate. The powder was 59 in iodine value, 8.5×10$^3$ in $\overline{Mn}$, 4.8×10$^4$ in $\overline{Mw}$ and 13.5 wt% in fluorine content. Accordingly, the above white powder was a prepolymer in which Compound A and diallyl phthalate were contained in molar ratio of 1:7.3. A casting plate was obtained in the same manner as in Example 4 with use of the prepolymer.

EXAMPLE 6

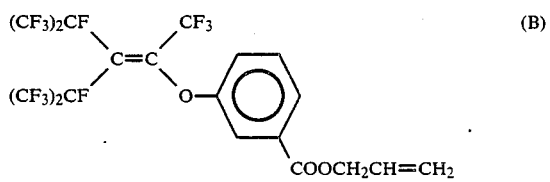

White powder (231 g) was obatined in the same manner as in Example 4 with use of Compound B (600 g), diallyl isophathalate (300 g), benzoyl peroxide (13 g), dibutyltin dilaurate (11 g) and water (450 ml). The powder was 55 in iodine value, 8.8×10$^3$ in $\overline{Mn}$, 8.8×10$^4$ in $\overline{Mw}$ and 20.6 wt% in fluorine content. Accordingly, the above white powder was a prepolymer in which Compound B and diallyl isophthalate were contained in molar ratio of 1:3.9. A casting plate was prepared in the same manner as in Example 4 with use of the prepolymer.

EXAMPLE 7

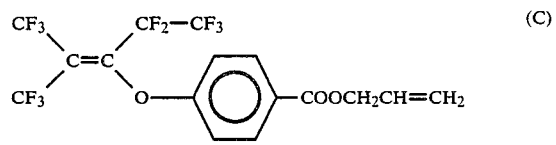

White powder (162 g) was obatined in the same manner as in Example 4 with use of Compound C (460 g), diallyl terephathalate (250 g), benzoyl peroxide (10 g), dibutyltin dilaurate (8.5 g) and water (350 ml). The powder was 54 in iodine value, 1.1×10$^4$ in $\overline{Mn}$, 1.3×10$^5$ in $\overline{Mw}$ and 19.5 wt% in fluorine content. Accordingly, the above white powder was a prepolymer in which Compound C and diallyl terephthalate were contained in molar ratio of 1:2.5. A casting plate was prepared in the same manner as in Example 4 with use of the prepolymer.

COMPARISON EXAMPLE 1

Into diallyl terephthalate (50 parts) was dissolved 50 parts of diallyl phthalate prepolymer [trade name, DAISO DAP A, Osaka Soda Co., Ltd., $\overline{Mn}$=6.7×10$^3$, $\overline{Mw}$=2.6×10$^4$, iodine value 61] and benzoyl peroxide (2 parts) was added thereto. A casting plate was prepared in the same manner as in Example 4 with use of the mixture.

COMPARISON EXAMPLE 2

A casting plate was prepared in the same manner a in Comparison Example 1 except that diallyl terephthalate polymer [trade name, DAPREN, Osaka Soda Co., Ltd., $\overline{Mn}=7.3\times 10^3$, $\overline{Mw}=2.5\times 10^5$, iodine value 51] was used in place of DAISO DAP A.

Casting plates prepared in Examples 4 to 7 and Comparison Example 1 and 2 were checked for water absorbency at 23° C. according to JISK-6911. The results were given in Table 1.

TABLE 1

|       | Water absorbency (wt %) |          | Water absorbency (wt %) |
| ----- | ----------------------- | -------- | ----------------------- |
| Ex. 4 | 0.02                    | Ex. 7    | 0.05                    |
| Ex. 5 | 0.07                    | Com. Ex. 1 | 0.33                  |
| Ex. 6 | 0.03                    | Com. Ex. 2 | 0.41                  |

We claim:

1. A perfluoroalkenyloxybenzoic acid derivative of the formula

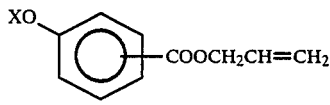
(1)

wherein X is perfluoroalkenyl group having 6 to 14 carbon atoms.

2. A process for preparing a perfluoroalkenyloxybenzoic acid derivative of claim 1 which comprises reacting an allyl alcohol with a perfluoroalkenyloxybenzoic acid of the formula

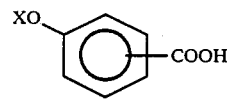
(3)

wherein X is same as above.

3. A process for preparing a perfluoroalkenyloxybenzoic acid derivative of claim 1 which comprises reacting a perfluoroalkene XF with allyl hydroxybenzoate of the formula

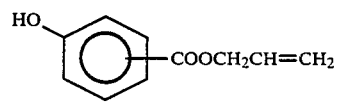
(4)

wherein X is same as above.

4. A prepolymer of a perfluoroalkenyloxybenzoic acid derivative comprising a repeating unit of the formula

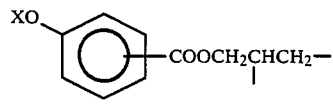
(2)

wherein X is perfluoroalkenyl group having 6 to 14 carbon atoms, and a repeating unit having one double bond and derived from the cleavage of double bond of a diene compound.

5. A prepolymer as defined in claim 4 wherein at least one % by weight of the repeating unit of the formula (2) is contained in the prepolymer.

6. A prepolymer as defined in claim 4 wherein the diene compound is at least one selected from the group consisting of diallyl phthalate, diallyl isophthalate and diallyl terephthalate.

* * * * *